United States Patent [19]

Kloots

[11] 3,951,139

[45] Apr. 20, 1976

[54] FIBEROPTIC HEADLIGHT

[75] Inventor: Jacobus Kloots, Sturbridge, Mass.

[73] Assignee: Applied Fiberoptics, Incorporated, Southbridge, Mass.

[22] Filed: Oct. 7, 1974

[21] Appl. No.: 512,627

[52] U.S. Cl. ................................... 128/23; 240/59
[51] Int. Cl. ........................................... A61b 1/06
[58] Field of Search ................. 128/22, 23; 240/59, 240/60, 67, 68, 70, 81 BD, 41.15, 1.4, 52

[56] References Cited
UNITED STATES PATENTS

| 2,176,789 | 10/1939 | Capitani | 240/59 |
| 3,185,838 | 5/1965 | Warshawsky | 240/73 X |
| 3,191,023 | 6/1965 | Sullivan et al. | 240/41.15 |
| 3,645,254 | 2/1972 | Burton | 128/23 |
| 3,745,993 | 7/1973 | Feinbloom | 128/23 |
| 3,830,230 | 8/1974 | Chester | 128/23 |

Primary Examiner—Lawrence Charles
Attorney, Agent, or Firm—Thomas N. Tarrant

[57] ABSTRACT

A headlamp in which the optical unit receives light through a fiberoptic light conductor, the unit being readily manipulable by rotation about a vertical axis and a horizontal axis and by direct up and down vertical movement. A "joystick" projecting from the top of the optical unit provides a handle for manipulation.

5 Claims, 3 Drawing Figures

FIBEROPTIC HEADLIGHT

BACKGROUND OF THE INVENTION

1. Field of the Invention

The present invention relates to lamps for surgeon's headbands and particularly to those using fiberoptics to inject the light from a remote source.

2. Description of the Prior Art

In a lamp to be supported on a person's head, optimum efficiency would be obtained if the beam could originate exactly between the person's eyes. This would reduce troublesome shadow effects and parallax problems. A headlight as disclosed by Wallace in U.S. Pat. No. 3,285,242 is compact and can be readily manipulated for positioning between the eyes. However, the on-axis entrance Wallace uses for his fiberoptic cable as well as his double ball and socket joint arrangement require that the optical unit be supported a distance in front of the eyes. For minimum visual interference, the optical unit would have to extend a much shorter distance in front of the bridge of the nose. The arrangement disclosed by Rodel in U.S. Pat. No. 2,539,104 would seem to have better possibilities, but Rodel apparently failed to recognize the desirability of close proximity, or was required to maintain a distance due to heat from his integral light source.

SUMMARY OF THE INVENTION

In accordance with the present invention a fiberoptic headlight is provided which is vertically positionable in close proximity to the bridge of the wearer's nose and is rotatably adjustable about two mutually perpendicular axes. Vertical positioning and rotation about a vertical axis are both provided by a cylindrical shaft frictionally restrained in a cylindrical guideway by adjustable compression of an elastomeric annular ring. The fiberoptic entrance is at the top near the back and a hinged joint to the vertical shaft is directly in back of the fiberoptic entrance allowing close proximity to the wearer's forehead. To aid in adjustment, an autoclavable handle is provided in the form of an elongated pin projecting from the top front of the optical unit and angling forward. Thus, it is an object of the invention to provide a surgeon's headlamp that has an optical unit adjustable for placement substantially between the eyes.

A further object is to provide a fiberoptic headlamp that is readily adjustable both vertically and about two mutually perpendicular axes.

A further object is to provide a fiberoptic headlamp that has adjustable frictional restraint of motion in both up and down and rotational directions by a single compressed elastomeric ring.

Still, a further object of the invention is to provide a fiberoptic headlamp with a control for multidirectional positioning.

Further objects and features of the invention will become apparent upon reading the following description together with the Drawing.

DESCRIPTION OF THE PREFERRED EMBODIMENT

Figure 1:
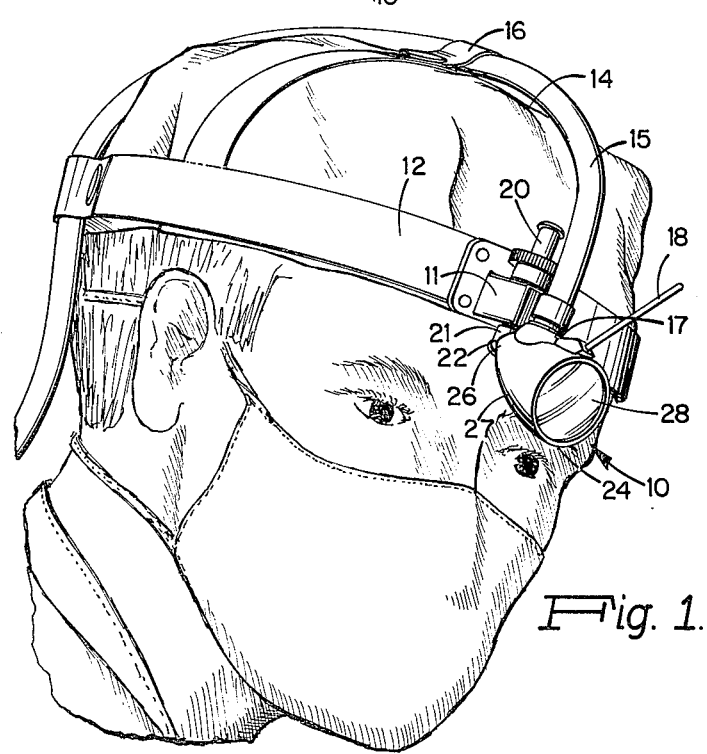
FIG. 1 is a perspective view of a headlamp in accordance with the invention depicted on a surgeon's head.

A headlamp that can be positioned to provide a light beam substantially coaxial with human vision must have a compact optical unit that is supported with minimal horizontal displacement from the headband. FIG. 1 depicts optical unit 10 supported by mounting 11 from headband 12 worn on head 14 of a doctor. Fiberoptic cable 15, supported in conventional manner at strap 16 of headband 12 connects to optical unit 10 with a usual snap-in connector 17 in the top-rear wall of optical unit 10. The beam direction is readily adjustable by hand using "joystick" 18 projecting forward and upward from the top-front wall of optical unit 10.

Figure 2:
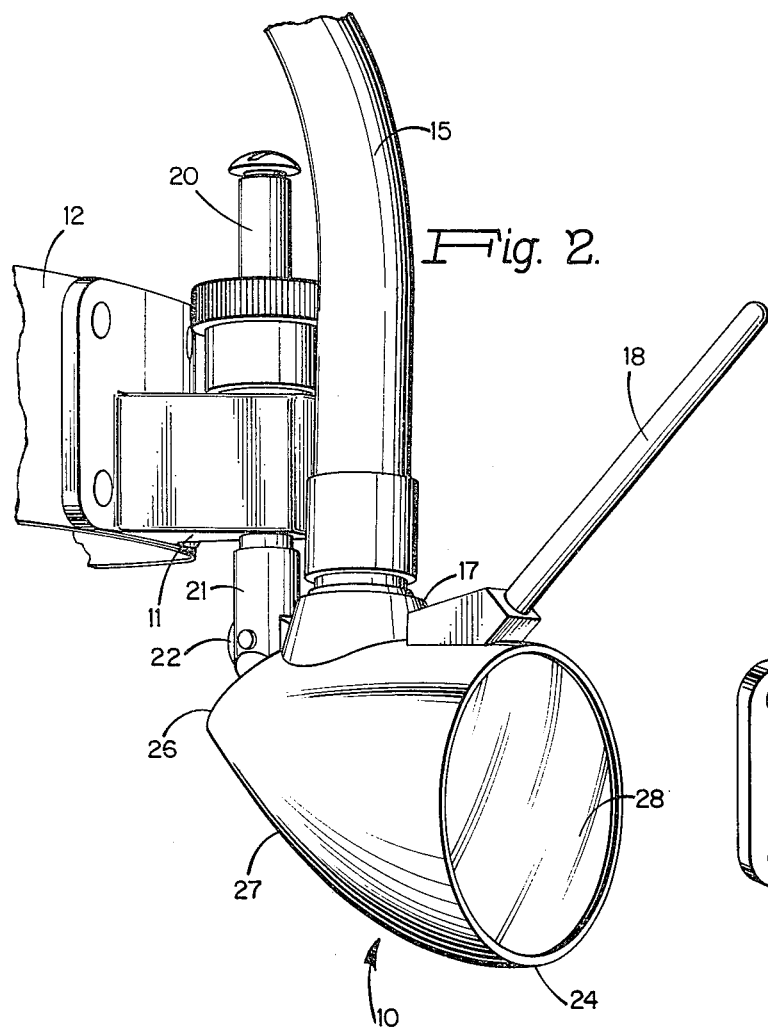
FIG. 2 is a perspective view of a headlamp assembly according to the invention.
Figure 3:
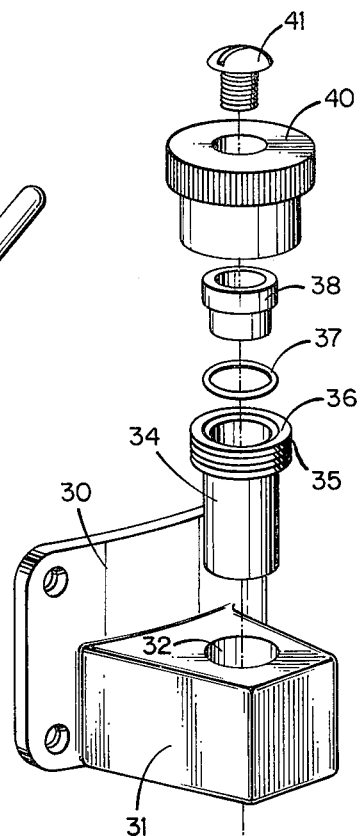
FIG. 3 is an exploded view of the mounting elements of FIG. 2.

Headlamp unit 10 is better shown in FIG. 2 secured on mounting 11. FIG. 3 depicts the elements of mounting 11 in exploded detail to help in understanding the operation. Shaft 20, as depicted in FIG. 2, is split at bottom end 21 to pass over projecting "ear" 22 of optical unit housing 24. Screw 25 passing through split end 21 and a hole in ear 22 secures optical unit 10 to shaft 20. Tension on screw 25 pinches split end 21 against ear 22 as a frictional damper on up and down rotation of unit 10 around screw 25. Housing 24 is wedgeshaped at the rear, the upper slanted surface 26 rising to meet connector socket 17 and lower slanted surface 27 angling forward toward the bottom of output lens 28. Ear 22 projects from surface 26 so that shaft 20 is secured to housing 24 slightly forward of the back of unit 10 and just behind connector 17.

Referring particularly to FIG. 3, flange 30 is a slightly curved flange adapted for mounting to headband 12 (FIG. 1). Projecting from flange 30 is support element 31 which together with flange 30 makes up mounting 11. Mounting 11 is suitably cast or molded from metal or plastic. Support element 31 is bored with a cylindrical passage 32. Press fitting 34 is a tube with an enlarged and threaded upper segment 35. Fitting 34 is press-fit into passage 32. The top of segment 35 has annular recess 36 for receiving an elastomer ring such as O-ring 37. Recess 36 also partially accomodates bushing 38 which fits against the upper surface of O-ring 37. Through-bored capnut 40 has an interior screw thread (not illustrated) matching threaded segment 35 and an interior annular ridge (not illustrated) for abutting the upper rim of bushing 38.

In assembly, fitting 34 is pressed into element 31 and shaft 20 is passed up through fitting 34. O-ring 37, bushing 38 and nut 40 are passed down over the upper end of shaft 20 and screw 41 is threaded into the top end of shaft 20 to prevent shaft 20 from passing back through nut 40. Nut 40 is then threaded down onto fitting 34 forcing bushing 38 against O-ring 37. The pressure against O-ring 37 forces it to expand against shaft 20 acting as a friction damper on movement of shaft 20. Thus, the freedom with which shaft 20 may be moved up and down or rotated within fitting 34 is controlled by adjustment of nut 40.

Referring once again to FIG. 2, housing 24 of optical unit 10 is suitably cast or molded from plastic or metal. It contains a reflector (not illustrated) such as a mirror or prism resting against slanted bottom side 27 so that is intercepts light from the direction of connector 17 and directs it out through lens 28.

In front of connector 17 at the top of housing 24 is mounted "joystick" 18. "Joystick" 18 is suitably a metal rod about ½ cm in diameter and 4 to 6 cm in length for ready fingertip grasping. For purposes of leverage in the different desired directions, it is depicted as angled forward and upward at about 45° from the optical axis of lens 28.

In operation, headband 12 carrying optical unit 10 is placed on a user's head and optical cable 15 is connected into a separate light source. The user adjusts optical unit 10 by first sliding shaft 20 downward as close to a central point between the eyes as possible without undue interference with vision. Next optical unit 10 is angled by means of joystick 18 so that the beam coincides with vision at the point of interest.

While the invention has been described with respect to a specific embodiment, obvious variations are contemplated as within the scope of the invention and it is the intent to cover the invention as set forth within the scope of the appended claims.

I claim:
1. A manipulatable fiberoptic headlamp in which the optical unit is positionable in close proximity to the bridge of the wearer's nose and is rotatably adjustable about two perpendicular axes by a joystick comprising:
   a. an optical unit comprising:
      1. a housing having a wall, a front aperture and a back;
      2. a connector in the wall of said housing for receiving a fiberoptic light conducting cable.
      3. lens means mounted in said front aperture for transmission of light received through said connector;
      4. a control rod mounted to said wall adjacent said connector angling toward said front aperture and away from said housing; and,
      5. a hinge connection at the back of said housing;
   b. a support member comprising:
      1. a flange portion for mounting to a headband;
      2. a body portion defining a cylindrical passage;
      3. a recess around an end of said passage carrying an annular elastomeric ring; and,
      4. threadably adjustable means mounted to said body portion and compressibly bearing against said ring;
   c. a cylindrical post connected at one end to said hinge connection and passing through said cylindrical passage being frictionally retained in said passage by said elastomeric ring, whereby said control rod can be manipulated to rotate said optical unit up and down about said hinge connection and to rotate said optical unit back and forth about the axis of said post.

2. A manipulatable fiberoptic headband lamp according to claim 1 wherein said rod extends at an angle of substantially 45° above the axis of illumination of said lamp and is in the range of 4 to 6 cm long.

3. A manipulatable fiberoptic headband lamp according to claim 1 wherein said hinge connection is pinned by a screw, whereby said screw can be tightened to adjust the resistance to up and down swinging of said housing about said hinge connection.

4. A manipulatable fiberoptic headband lamp according to claim 3 wherein the back of said housing terminates in a wedge-shape formed by a first inclined plane starting at the top and inclined downward and rearward and a second inclined plane starting at the bottom and inclined upward and rearward to meet said first inclined plane at a point above the horizontal central plane of the housing and an "ear" extends upward from said first inclined plane for receiving a forked bottom end of said post in order to form said hinge.

5. A manipulatable fiberoptic headband lamp according to claim 1 wherein said cylindrical passage comprises an insert in said support member, said insert having an upward projection bearing an exterior screw thread, said adjustable means comprising a bushing bearing against said ring and a nut threadable down on said exterior screw threads and bearing against said bushing.

* * * * *